(12) United States Patent
Bitoun (10) Patent No.: US 9,180,208 B2
(45) Date of Patent: Nov. 10, 2015

(54) COMPOSITION AND METHODS FOR ENHANCING SURFACE REFLECTANCE

(71) Applicant: i SONIC Medical Corporation, Paris (FR)

(72) Inventor: Pierre Bitoun, Paris (FR)

(73) Assignee: i SONIC Medical Corporation, Paris (FR)

( * ) Notice: Subject to any disclaimer, the term of this patent is extended or adjusted under 35 U.S.C. 154(b) by 0 days.

(21) Appl. No.: 14/037,211

(22) Filed: Sep. 25, 2013

(65) Prior Publication Data

US 2015/0086630 A1    Mar. 26, 2015

(51) Int. Cl.
| | |
|---|---|
| *A61K 49/00* | (2006.01) |
| *A61K 9/16* | (2006.01) |
| *A61K 9/00* | (2006.01) |
| *A61B 5/00* | (2006.01) |
| *C03C 12/02* | (2006.01) |

(52) U.S. Cl.
CPC ........... *A61K 49/0013* (2013.01); *A61B 5/0093* (2013.01); *A61K 9/0048* (2013.01); *A61K 9/1652* (2013.01); *A61K 49/0004* (2013.01); *C03C 12/02* (2013.01); *C03C 2201/02* (2013.01)

(58) Field of Classification Search
None
See application file for complete search history.

(56) References Cited

U.S. PATENT DOCUMENTS

| | | | |
|---|---|---|---|
| 5,900,978 A | 5/1999 | Sagar et al. | |
| 6,242,056 B1 | 6/2001 | Spencer et al. | |
| 6,482,519 B1 | 11/2002 | Schleifstein | |
| 6,525,111 B1 | 2/2003 | Spencer et al. | |
| 6,555,526 B2 * | 4/2003 | Matsuo et al. | 514/53 |
| 2007/0175283 A1 | 8/2007 | Nelson et al. | |
| 2010/0121442 A1 * | 5/2010 | Shea et al. | 623/6.11 |
| 2012/0219606 A1 | 8/2012 | Deckner et al. | |

OTHER PUBLICATIONS

Lee et al., "Engineered microsphere contrast agents for optical coherence tomography", Optics Lett., 28(17), pp. 1546-1548 (2003).*
3M; http://solutions.3mcanada.ca/wps/portal/3M/en_CA/CA_VIS/Home/mai . . . ; Copyright 3M, 2013.
Prizmalite; http://prizmalite.com/main/about/; Copyright 2012-2013.
International Search Report and Written Opinion regarding corresponding PCT Application No. PCT/IB2014/003087, dated May 7, 2015.

(Continued)

*Primary Examiner* — Bethany Barham
*Assistant Examiner* — Barbara Frazier
(74) *Attorney, Agent, or Firm* — Lewis & Reese, PLLC (57) ABSTRACT

Microspheres, typically sterile, inert, silica glass microspheres, are dispersed in a carrier suitable for use relative to the object to be imaged and analyzed. In the case of ophthalmic imaging, an ophthalmically-acceptable gel is used and the resulting composition is dispensed into a mammalian eye. The gel and microspheres dispersed therein coat and conform to the surface of the eye. The microspheres enhance reflectance from the eye which improves signal-to-noise ratio and improves imaging quality.

25 Claims, 7 Drawing Sheets

(56) References Cited

OTHER PUBLICATIONS

Ehlers, Justis P. et al., "Evaluation of Contrast Agents for Enhanced Visualization in Optical Coherence Tomography," Investigative Ophthalmology & Visual Science 2010 Association for Research in Vision and Ophthalmology Inc. USA, vol. 51, No. 12, Dec. 2010, pp. 6614-6619.

O'Donnell, Clare et al, "Grading of Corneal Transparency," Contact Lens & Anterior Eye, Stockton Press, Basingstoke, GB, vol. 27, No. 4, Dec. 1, 2004, pp. 161-170.

* cited by examiner

COMPOSITION AND METHODS FOR ENHANCING SURFACE REFLECTANCE

FIELD

Embodiments disclosed herein relate to compositions and methods for enhancing reflectance from a surface and, more particularly, to ophthalmic drops which enhance reflection of light from at least the cornea.

BACKGROUND

Light reflectance techniques are known for non-destructive analysis of object shapes, object and surface characteristics, responses of an object or surface to stimuli and the like. By way of example, interferometric techniques are known for analyzing damage to structural elements, such as beams. Similarly, microscopy and photography techniques of various types utilize transmission and reflectance of light from an object and are well known.

In the case of corneal integrity, it is known to use a dye, such as fluorescein to stain the cornea for visualizing abrasions, tears and the like in the cornea.

Further, it is well known to use reflection of incident light from the cornea as a tool for screening and diagnosis of a variety of corneal abnormalities and disorders, including but not limited to corneal dystrophies, keratoconus, strabismus and corneal integrity following chemical or heat burns or trauma to the eye. Further, reflection of simple light or laser light has been used in various interferometric and laser techniques for determining corneal thickness, shape and response to acoustic and other stimuli, such as is used in the determination of changes in intraocular pressure.

As with many other surfaces which may be analyzed using reflectance, it is problematic in such techniques that while the cornea does reflect some of the incident light, it is not an optimum surface for light reflectance techniques. Such techniques are therefore prone to significant noise issues which lead to poor signal-to-noise detection.

Where retro-reflection is utilized, such as in self-mixing laser techniques, the reliability and reproducibility of the results may be adversely affected by low reflectance from the cornea.

Clearly there is interest in improving the reflectivity of the cornea for improving signal-to-noise ratios in a variety of reflectance-based imaging techniques.

SUMMARY

Embodiments disclosed herein disperse silica glass microspheres in a carrier fluid for coating a surface of interest for enhancing reflectance therefrom. Embodiments are particularly useful where the surface is not naturally reflective or is not optimally reflective. A diameter of the microspheres is generally related to the size of the incident beam used for the imaging technique. The carrier fluid is typically selected to permit dispersion of the microspheres therein and for coating the surface of interest with the dispersed microspheres.

In embodiments which are used for imaging ex vivo tissues or inanimate objects, the carrier fluid is inert and is selected to be suitable for coating the surface without altering or otherwise damaging the properties of the surface or the underlying object.

In a broad aspect, for use in ophthalmic imaging, an ophthalmic composition comprises sterile, silica glass microspheres dispersed in an inert, ophthalmically-acceptable gel.

The diameter of the microspheres, while related to the size of the beam used for the imaging technique, is also selected so as to be tolerated in the mammalian eye without creating discomfort. The inert, ophthalmically-acceptable gel has a viscosity suitable for dispersing the microspheres therein and for remaining on the surface of the eye for sufficient time to allow completion of the imaging. In embodiments, the microspheres are added to the gel from about 5% w/v to about 50% w/v, from about 10% w/v to about 50% w/v, or from about 10% w/v to about 20% w/v.

In another broad aspect, a method for enhancing reflection from a corneal surface for imaging of the cornea using light reflectance comprises dispensing onto a mammalian eye, prior to the imaging, a composition comprising sterile, silica glass microspheres dispersed in an inert, sterile ophthalmically-acceptable gel.

The composition is vigorously mixed to disperse and suspend the microspheres in the gel prior to dispensing a drop into the eye. Mixing, while vigorous, must not be so vigorous as to change the viscosity of the gel. In embodiments, the composition is vortexed at about 3200 rpm for between about 5 to 10 minutes prior to use. Following imaging, the composition is rinsed from the eye at least once using an ophthalmically suitable rinse.

Once mixed, the composition can be used for an optimal time after which the microspheres are allowed to completely settle and the composition must be thereafter be remixed for subsequent use. In embodiments, the optimal time is about 5 minutes.

DETAILED DESCRIPTION

Applicant has used the terms "reflectance" and "reflectivity" interchangeably herein.

Spherical microbeads or microspheres are well known in the paint industry for use in making reflective tapes, reflective clothing, road signs and for enhancing color and the like. The microspheres utilize at least the principles of retro-reflection to enhance the brightness of the reflected light by reducing scatter and directing all of the reflected light toward the source of the incident light.

In embodiments disclosed herein, microspheres, such as sterile, inert silica glass microspheres available from Prizmalite Industries Inc. of New York, N.Y., USA are dispersed in a carrier fluid suitable for coating a surface to be analyzed using any variety of reflectance techniques. Such embodiments are particularly useful where the surface is not naturally reflective or optimally reflective. The carrier fluid is capable of dispersing the microbeads therein and of being retained on the surface for at least a time sufficient to obtain reflectance measurements or results therefrom.

In embodiments for application to inanimate surfaces such as structural beams and the like, the microbeads are dispersed in a carrier which adheres temporarily or permanently to the surface. The carrier may include, but is not limited to, viscous gels and clear adhesives such as cyanoacrylates and the like.

In embodiments for use in ophthalmic reflectance techniques, the silica glass microspheres are dispersed in an inert, ophthalmically-acceptable gel, suitable for use in coating the cornea of an eye for conforming thereto.

Embodiments are suitable for a wide variety of corneal imaging techniques where enhanced reflection from the cornea aids in improving image quality. Such techniques include, but are not limited to routine eye examination such as corneal slit lamp imaging for examining the anterior surface of the cornea for identification of corneal lesions, such as anomalies, foreign bodies, scars, trauma, tumors, infections, malformations, dysplasia or dystrophies of the cornea, laser imaging techniques such as retro-reflective laser imaging, Scheimpflug corneal imaging using a high speed camera and other reflectance-based imaging techniques.

Further, embodiments are suitable for imaging applications based upon reflectance from any tissue, material or substance using optical microscopy and photography of any kind Such applications include, but are not limited to, widefield microscopy, bright field microscopy, interference reflection microscopy, differential interference contrast microscopy, confocal microscopy and other forms of microscopy. The widespread applicability of embodiments described herein is possible by selecting an appropriate sized microsphere based upon the size of the sample to be analyzed and the wavelength of light used for imaging, so as to enhance image contrast, quality and luminance.

If the object to be analysed is not analyzed in vivo, the carrier can be any suitable carrier which will not alter or otherwise damage or change the characteristics of the surface upon which the composition is applied.

In Vivo Ophthalmic Imaging

In the case where embodiments are to be used for in vivo ophthalmic imaging, such as corneal imaging, the microspheres are dispersed in the ophthalmically-acceptable gel, such as by vigorous mixing. The gel acts to coat and conform to the corneal surface and retain the microspheres dispersed therein for a period of time sufficient to complete the imaging, despite blinking by the patient.

Suitable ophthalmic gels have a viscosity capable of dispersing and maintaining the microspheres therein on the surface of the eye, without allowing the microspheres to fall into the lower eyelid during imaging. If the gel is too thick however, it is not easily tolerated by the patient. Examples of two such suitable gels are trehalose gels, such as a 3% trehalose gel commercialized as THEALOZ® from Spectrum Theá Pharmaceuticals Limited and sodium carmellose gels, such as a 1% sodium carmellose gel commercialized as CELLUVISC® available from Allergan, Inc. As one of skill in the art will appreciate, if a gel is inert and ophthalmically-acceptable and has a viscosity which is suitable for dispersing and retaining the microspheres on the surface of the eye, the gel is likely to be suitable for use in embodiments disclosed herein. Further, the gel may contain other non-toxic auxiliary substances, such as anti-bacterial agents, anti-fungal agents, antioxidants, therapeutic molecules, preservatives and the like.

In embodiments, the gel can be used as a time-controlled application vehicle to apply specific therapeutic agents to the eye that cannot be applied to the cornea for more than a specified time in order to avoid toxic effects. The microspheres are then used as a tool to visualize whether any residual gel and therapeutic agent remains on the eye, such as following rinsing therefrom.

Embodiments are suitable for use with light in the visible spectrum as well as infrared light as suitable for ophthalmic use. One advantage to using infrared light is that it is inconspicuous and not visible to the patient.

Microsphere diameter is generally related to the size of the incident beam used for the imaging technique and to the size of the microsphere which can be tolerated in the mammalian eye without creating discomfort. Ideally, one wants the microspheres to be sufficiently small that a maximum number of reflective surfaces of the microspheres can be dispersed over the cornea and in the incident beam. If the microspheres are too small there is a greater tendency for the microspheres to group or clump.

By way of example, for an incident laser beam being 150 microns, microspheres having a diameter of about 10 to about 15 microns, about $\frac{1}{10}$th the diameter of the incident light beam, provide enhanced reflectance in a laser retro-reflectance technique. Using a 1550 nm IR laser, the size of the reflectance, visualized as a spot, is increased by 4 to 6 fold over that obtained without the microspheres. Should the laser beam be smaller than 150 microns, Applicant believes that for 10 to 15 micron diameter microspheres, there would be an insufficient number of microspheres within the laser beam to provide such an enhanced reflectance, the microspheres being simply too large for the beam diameter.

In an embodiment, using microspheres which range in diameter from about 6 microns to about 15 microns, Applicant believes that the microspheres can be added in a range of about 10% w/v to about 50% w/v. Amounts greater than about 50% w/v generally become too thick and are not well tolerated in the eye. At amounts less than about 10% w/v, there are insufficient microspheres dispersed in the gel to achieve enhanced reflectance sufficient to improve the imaging results. Further, Applicant believes that at or below about 5% w/v, the microspheres have a greater tendency to group or clump within the gel and are therefore much less effective.

General Preparation and Use for Ophthalmic Imaging

In embodiments, ophthalmic compositions are prepared using sterile techniques as is understood by those of skill in the art.

In an embodiment, an amount of sterile microspheres, such as the inert, silica glass microspheres, are weighed and added to a volume of sterile ophthalmic gel so as to result in a composition having from about 5% w/v to about 50% w/v microspheres therein. Prior to use, the composition is vigorously mixed to ensure uniform dispersion of the microspheres in the gel. As, over time, the microspheres will settle out of the gel, Applicant believes that there is an optimum time period in which the composition can be used for administration topically to at least one mammalian eye, after which the microspheres are no longer sufficiently dispersed within the gel.

In an embodiment, a composition comprising about 10% w/v microspheres having a diameter of about 6 to 15 microns was prepared. Applicant utilized a vortex at about 3200 rpm for a maximum of about 10 minutes to disperse the microspheres within the gel. In embodiments, the vortexing is between about 5 minutes to about 10 minutes. The timing of the vortexing is set so as to avoid altering the viscosity of the gel, such as causing the gel to liquefy, which would have adverse effect on the gel's ability to maintain the microspheres in a dispersion therein and to coat the surface of the eye.

In the 10% w/v example described above, the optimum time period in which the microspheres remain dispersed is about 5 minutes. After this time period, should the composition need to be used for administration topically to additional mammalian eyes, one must allow the microspheres to substantially completely settle, typically for an additional 5 minutes, before vigorously re-mixing the composition for applying topically in at least a second mammalian eye. Once again, the composition is usable within the optimal time period following the re-mixing, after which the steps of allowing the microspheres to settle followed by re-mixing are repeated for each subsequent period of use.

During the optimal time period in which the microspheres are dispersed in the gel, the composition is administered to mammalian eyes. Administration of the composition is typically as a droplet. In an embodiment, the droplet contains about 35 microliters of the composition.

After administration of a droplet into the eye and completion of the imaging, the composition is rinsed from the eye using at least one rinse with an ophthalmically-suitable rinse solution. In embodiments two or more rinses are used.

EXAMPLES

Microsphere Type

Applicant tested different types of microspheres to determine an optimum type for use in embodiments disclosed herein. Applicant believes that in prior art uses of microspheres, such as in signs and clothing, the microspheres are generally at least partially metallized, being typically half-metallized spheres.

A nude silica glass microsphere having a diameter of between 6 microns and 15 microns was compared to silica glass microspheres having a diameter between about 30 micron to about 100 microns and being half coated with aluminum (AL1), silica glass microspheres having a diameter between about 30 micron to about 100 microns and being half coated with aluminum treated with silane (AL2) and silica glass microspheres having a diameter between about 30 micron to about 100 microns and being half coated with aluminum treated with a fluorochemical (AL3). Each type of the microspheres were dispersed in CELLUVISC® ophthalmic gel to form a 20% w/v composition. The CELLUVISC® alone was used as a control.

Figure 1:
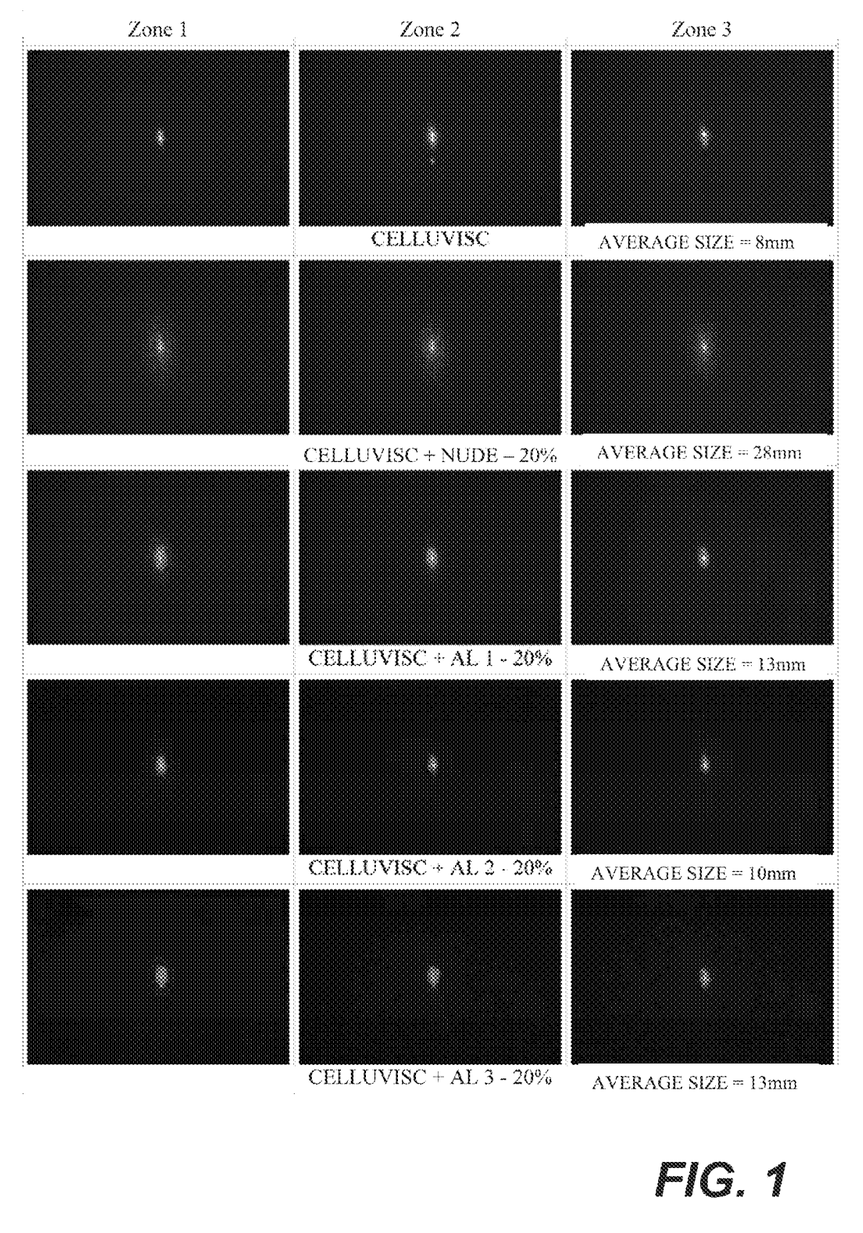
FIG. 1 are photographs illustrating a reflected laser beam from a droplet of a control, being a gel only, and a series of compositions comprising 20% w/v microspheres of a variety of types.

In a first test, a droplet of each composition, nude, AL1, AL2 and AL3, was placed on a glass plate and covered with an upper plate having a window formed therein above the droplet so as to avoid issues related to reflection from irregularities of the upper surface of the droplet. An infrared laser beam (1550 nm), being about 150 microns in diameter was directed at three separate zones in each droplet. The results are shown in FIG. 1 and the average reflectance size are itemized in Table A below.

TABLE A

| Composition | Average reflectance size for Zone 1, Zone 2 and Zone 3 |
| --- | --- |
| CELLUVISC ® | 8 mm |
| CELLUVISC ® + 20% nude | 28 mm |

TABLE A-continued

| Composition | Average reflectance size for Zone 1, Zone 2 and Zone 3 |
| --- | --- |
| CELLUVISC ® + 20% AL1 | 13 mm |
| CELLUVISC ® + 20% AL2 | 10 mm |
| CELLUVISC ® + 20% AL3 | 13 mm |

Figure 2:
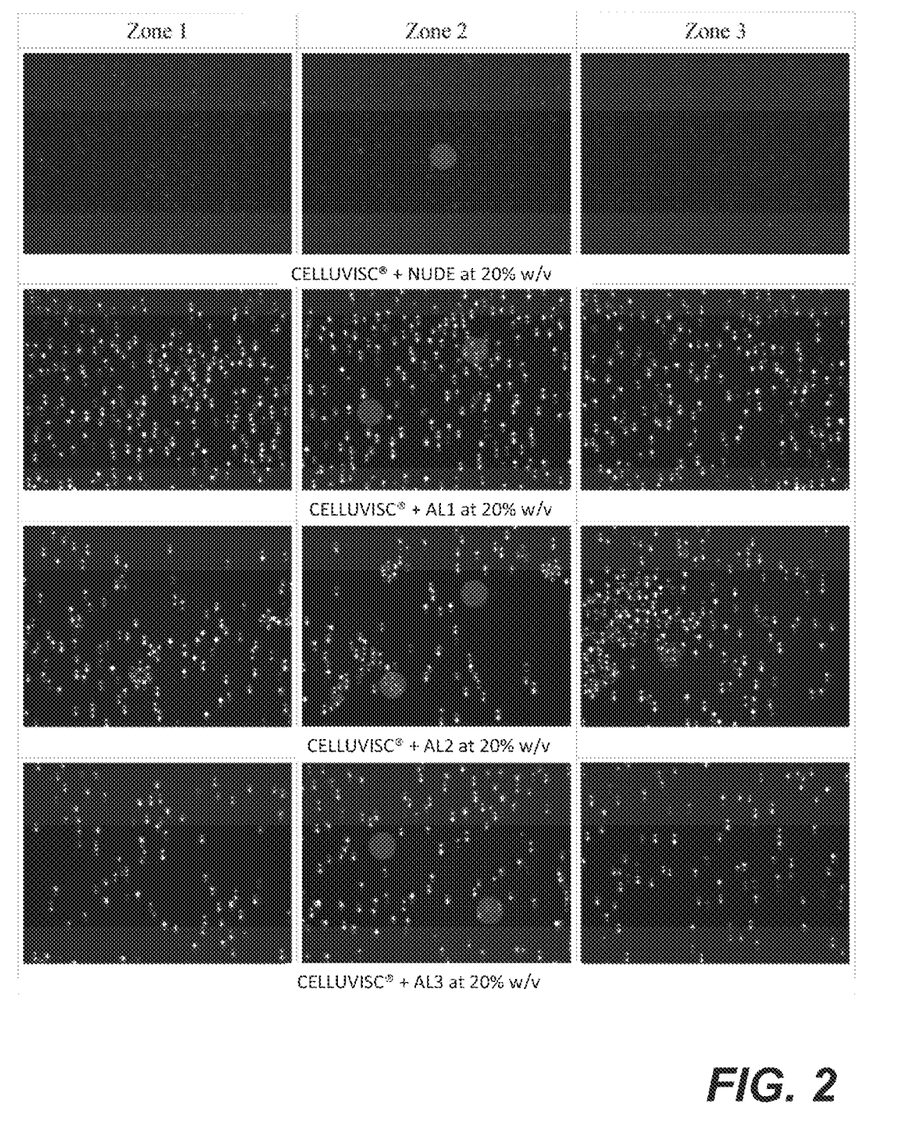
FIG. 2 are photographs of a droplet of each of the compositions of FIG. 1 taken through a microscope to illustrate microsphere dispersion for each of the gel and the series of compositions.

In a second test, a microscope enabled with a camera was used to observe the distribution of the microspheres in the CELLUVISC®. A Sony SX 910 (1280×960 pixels) digital camera was mounted on the microscope having a 10× objective and a 40 mm extension ring. The size of the zone observed was about 1.46 mm by 1.07 mm. The results are shown in FIG. 2. The red spot is the laser beam.

In all cases, the reflectance is enhanced. The greatest enhancement, being about 3 times, is seen with the nude silica glass microspheres. AL2 exhibits the lowest enhancement and thus, are considered to be unsuitable for embodiments disclosed herein. Applicant believes that based on the second test, a larger laser beam must be used to impact the same number of microspheres and a subsequent test with AL1 and AL3 should be performed in a rabbit eye.

Tests in Rabbit Eye

Figure 3:
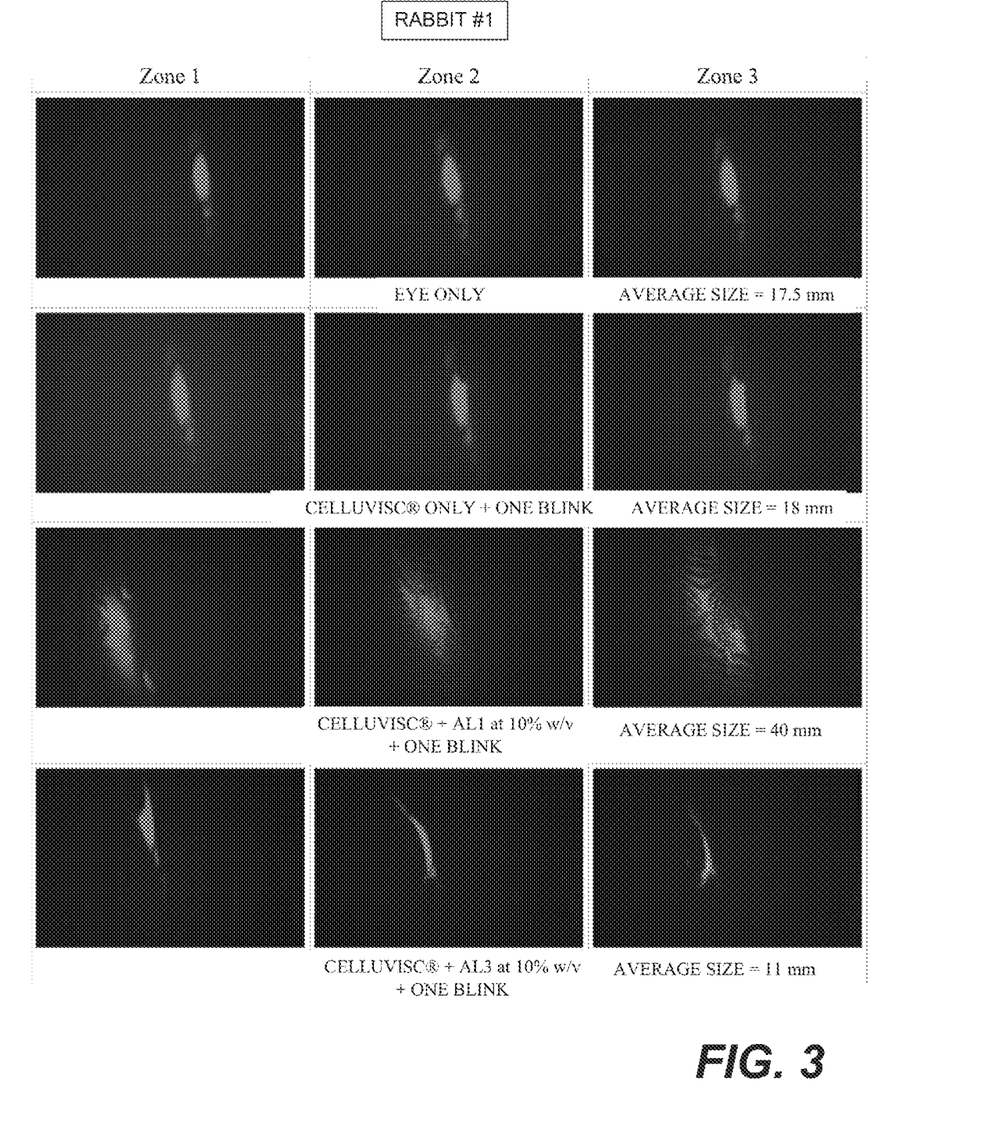
FIG. 3 are photographs illustrating a reflected laser beam from a rabbit eye for the eye only, for the gel only, and for two compositions comprising 10% w/v microspheres for two of the types of microspheres.

The metallized microspheres, AL1 and AL3, were tested in an eye of a dead rabbit. CELLUVISC® was used to disperse the microspheres and to coat and hydrate the rabbit eye. A composition comprising 10% w/v of each of the AL1 and AL3 was prepared. The rabbit head was obtained about 2.5 hours prior to the test by garroting the rabbit to maintain eye pressure. The head was stored at 6° C. Prior to the application of the compositions, the eyes were rinsed with physiological saline. A single drop of each composition AL1, AL3 was applied topically to the upper portion of the eye and the upper lid was lowered once. A HeNe laser having a beam diameter of 150 micron was focused on the eye and reflectance was observed on a white screen and photographed with a Nikon 80 camera. The camera was set at a zoom of 70, a focal point of 0.38 m, an aperture of F4.5, an exposure time of 20 seconds and a sensitivity of 1600 ISO. The images permitted conversion to pixels and each of the reflectance images was measured at the largest extent and the average taken. The results are shown in FIG. 3 and are itemized in Table B below.

TABLE B

| Composition | Average reflectance size for Zone 1, Zone 2 and Zone 3 |
| --- | --- |
| Eye alone | 17.5 mm |
| CELLUVISC ® alone with 1 blink | 18 mm |
| CELLUVISC ® + 10% AL1 with 1 blink | 40 mm |
| CELLUVISC ® + 10% AL3 with 1 blink | 11 mm |

Applicant notes that AL1 produces the largest reflectance. The AL3 microspheres show a deformation in the shape while also making the reflectance spot narrower, which Applicant believes is likely due to poor distribution of the microspheres and gel on the eye.

Figure 4:
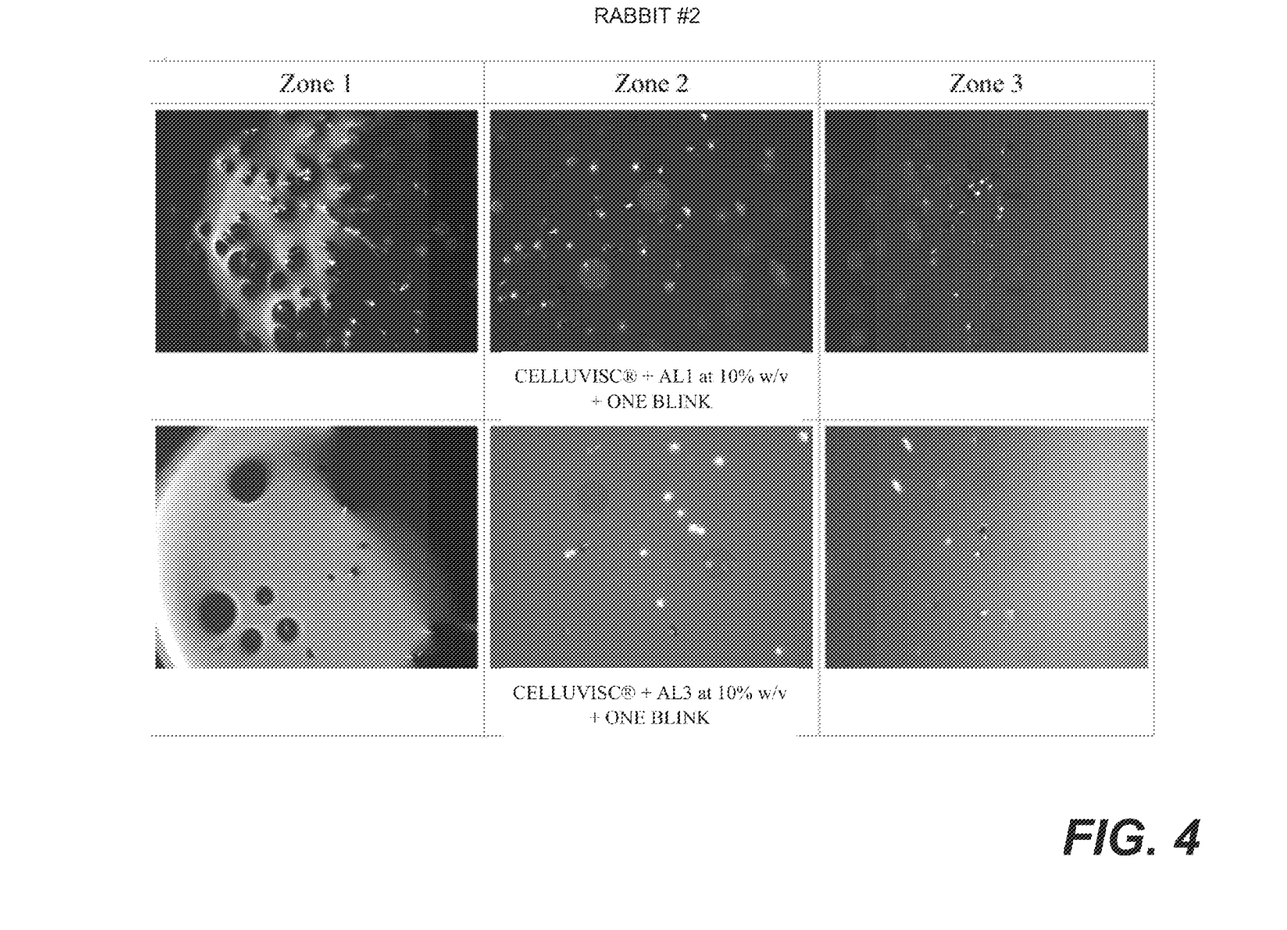
FIG. 4 are photographs of the rabbit eye of FIG. 3 taken through a microscope to illustrate microsphere dispersion for the two compositions.

In a second rabbit eye, the same microscope and Sony camera arrangement as previously described for the glass plate study was used to observe the distribution of the microspheres on the rabbit eye. The field that was observed was 1.46 mm by 1.07 mm. The results are shown in FIG. 4. The red spot is the 150 micron laser beam.

In the case of AL3, the microspheres are poorly distributed over the eye and the probability of being contacted by the laser beam is low. In the case of AL1, there is a visible improvement in reflectance however the distribution over the eye is still poor. Overall, Applicant believes that AL3 are unsatisfactory for the purposes of embodiments disclosed herein.

Ultimately, Applicant determined that the nude, 6 to 15 micron, inert silica glass microspheres provided sufficient enhanced reflectance and were well distributed within the gel and thus, over the surface of the cornea.

Effective Low End concentration of Microspheres

Figure 5:
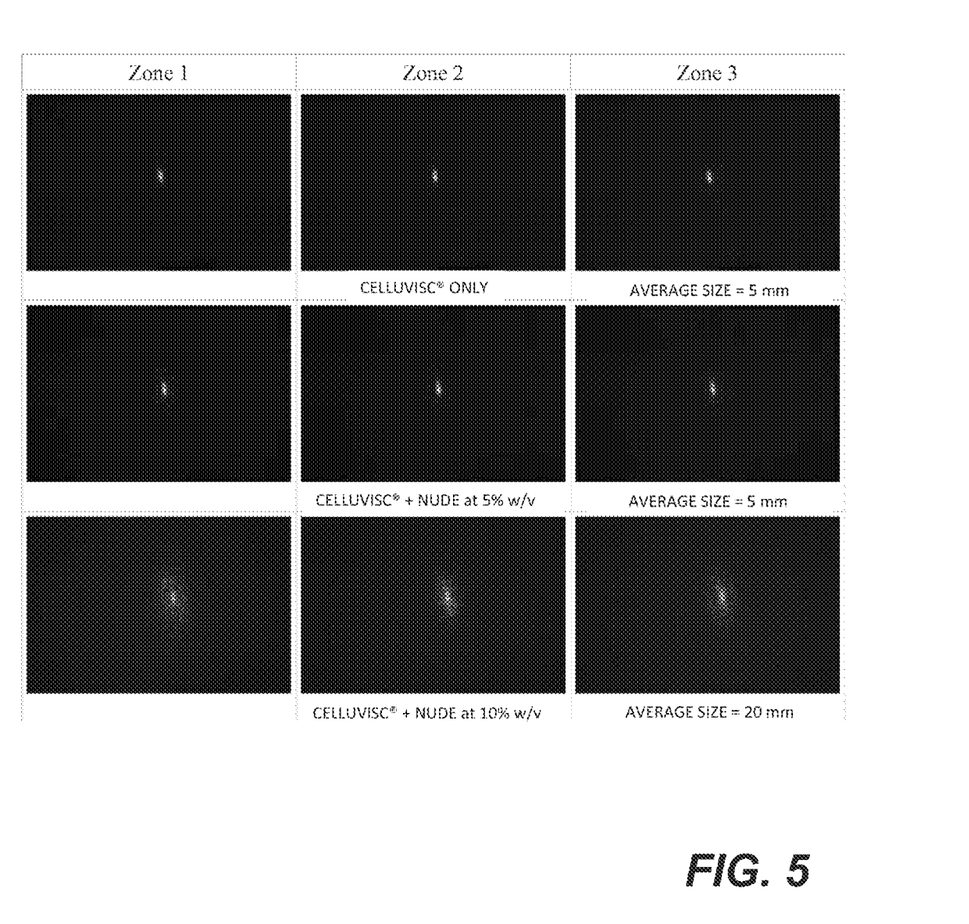
FIG. 5 are photographs illustrating a reflected laser beam from droplets of the gel only, and for compositions prepared using nude microspheres at 5% w/v and 10% w/v.

Compositions were prepared at 5% w/v and 10% w/v of the inert, silica glass microspheres in CELLUVISC®. A droplet was placed on a glass plate and an upper plate having a window therein was positioned with the window over the droplet to avoid reflectance issues caused by irregularity in the upper surface of the droplet. A HeNe laser was used to direct a 150 micron laser beam at the droplet and reflectance was observed on a white screen. Images were taken with a Nikon D80 camera set at a zoom of 50, a focal point of 0.5 m, an aperture of F4.5, and exposure time of 20 s and a sensitivity of 1600 ISO. The results are shown in FIG. 5 and are itemized in Table C below.

TABLE C

| Composition | Average reflectance size for Zone 1, Zone 2 and Zone 3 |
|---|---|
| CELLUVISC ® alone | 5 mm |
| CELLUVISC ® + 5% nude | 5 mm |
| CELLUVISC ® + 10% nude | 20 mm |

As can be seen the 5% w/v composition is less effective in enhancing reflectance than the 10% w/v composition.

Figure 6:
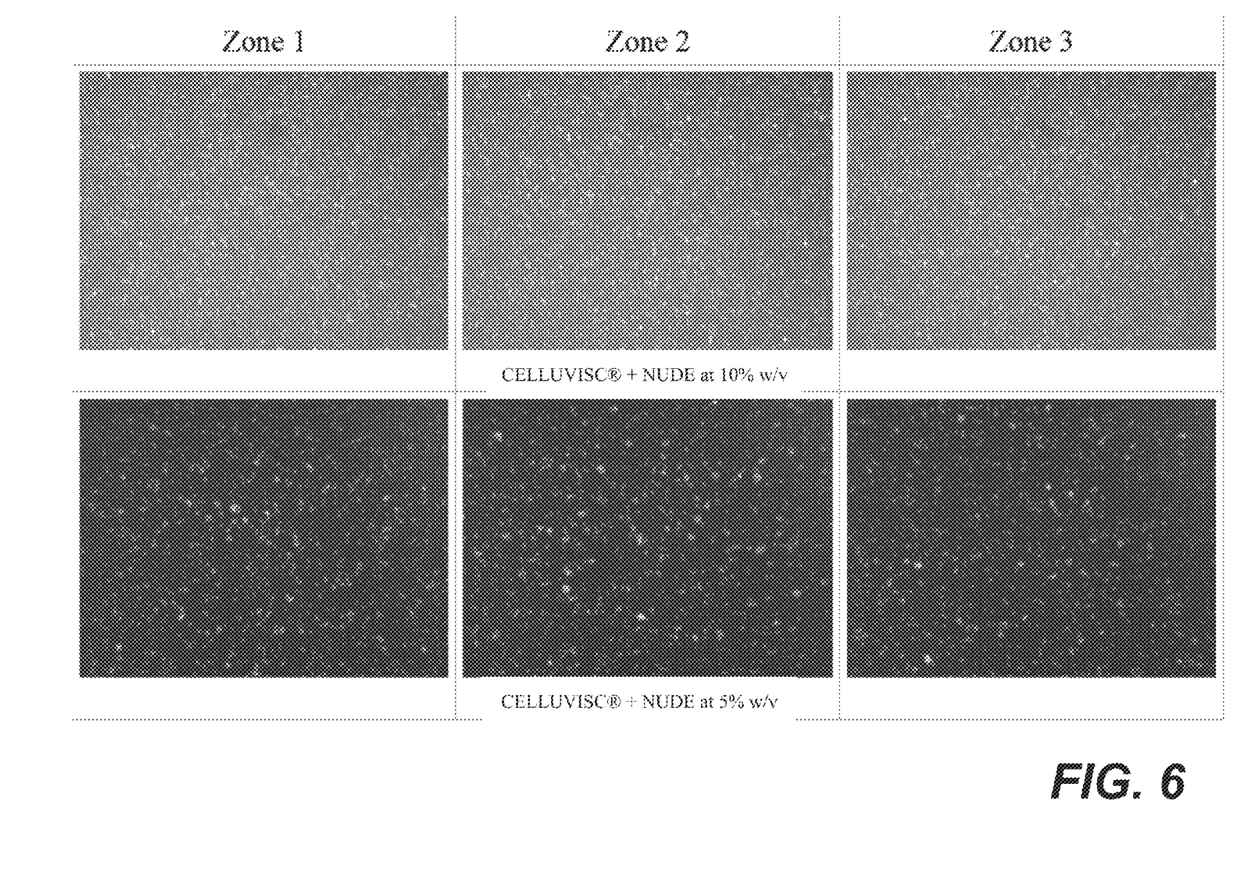
FIG. 6 are photographs taken through a microscope of the two composition of nude microspheres of FIG. 5.
Figure 7:
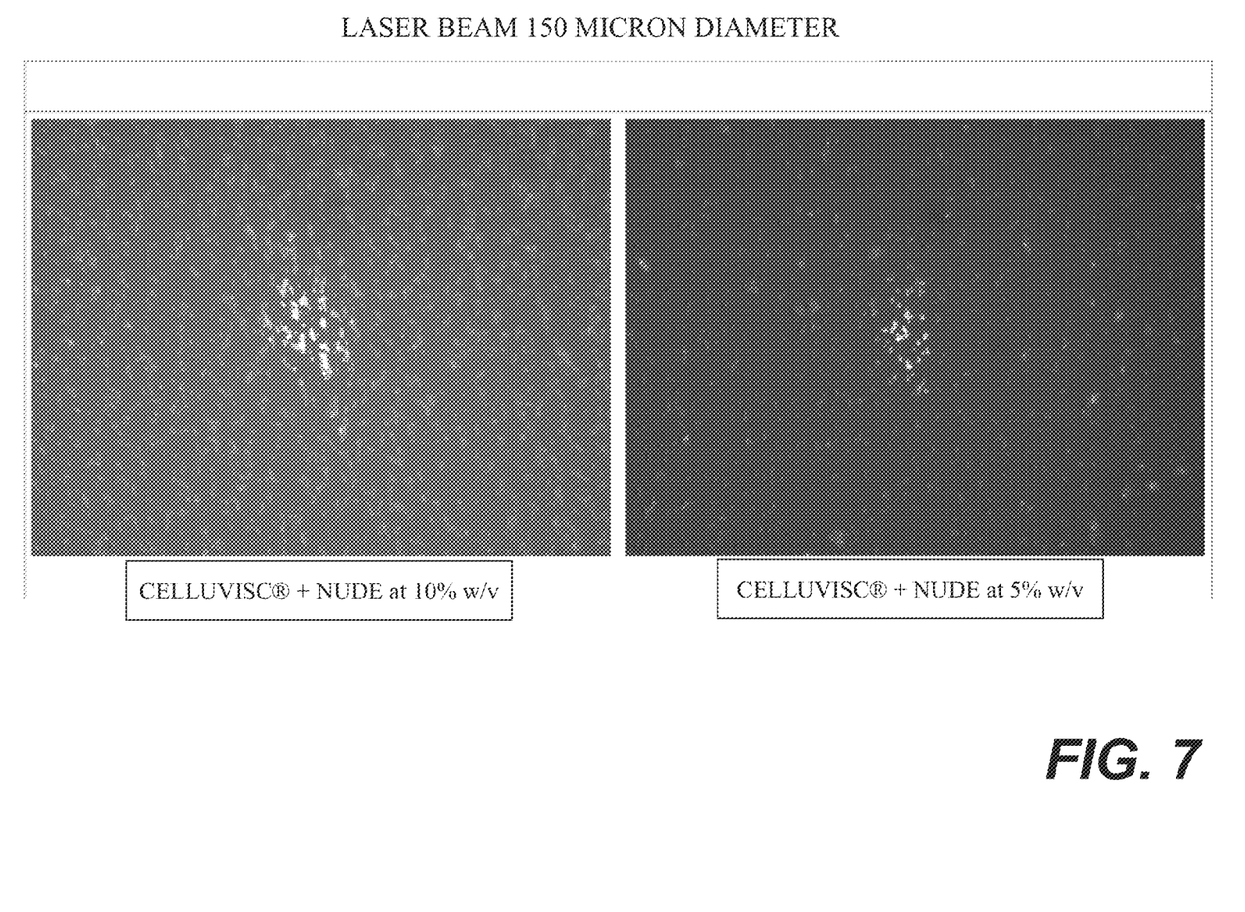
FIG. 7 are photographs of the two compositions of FIG. 5 illustrating reflectance using a laser beam having a diameter of 150 microns.

Having reference to FIGS. 6 and 7, the camera and microscope arrangement previously described was used to observe the distribution of the microspheres in the gel. The field observed was 1.46 mm by 1.07 mm.

The microspheres in the 5% w/v composition show a greater tendency to group or clump and are less evenly distributed than in the 10% w/v composition and the composition having 5% w/v is much less effective than the 10% w/v composition.

Ocular Irritation Studies

Using approved and regulated good laboratory practice (GLP) directives for animal testing, multiple applications of 35 microliters of a composition according to embodiments described herein were made in one eye of live albino rabbit subjects and of a placebo (CELLUVISC®) in the other eye. Each administration was immediately followed by blinking and was followed 15 minutes thereafter by triple rinsing with 0.9% NaCl (3×100 microliters). The eyes of the rabbits were observed using slit-lamps prior to testing and at intervals over the period of testing. The observations were scored using known scoring scales such as McDonald-Shadduck's scale and Draize's scale.

Slight conjunctival congestion was observed in all animals 15 minutes after rinsing the composition from the eyes. Generally the composition tested was macroscopically well tolerated as was the placebo.

What is claimed is:

1. An ophthalmic composition comprising microspheres of sterile, silica glass that enhance reflectance of light from a corneal surface of an eye, dispersed in an inert, ophthalmically-acceptable gel having a viscosity suitable for conforming to at least the corneal surface of the eye and dispersing the microspheres thereover, wherein the composition comprises about 10% w/v or greater of the silica glass microspheres.

2. The composition of claim 1 wherein the microspheres have a diameter adapted to be relative to a diameter of an incident light beam used for corneal imaging.

3. The composition of claim 2 wherein the microspheres have a diameter at least about 1/10th the diameter of the incident light beam.

4. The composition of claim 1 wherein the silica glass microspheres have a diameter less than about 30 microns.

5. The composition of claim 1 wherein the silica glass microspheres have a diameter of between about 6 microns and about 15 microns.

6. The composition of claim 1 wherein the composition comprises from about 10% w/v to about 50% w/v of the silica glass microspheres.

7. The composition of claim 5 wherein the composition comprises about 10% w/v to about 20% w/v of the silica glass microspheres.

8. The composition of claim 1 wherein the silica glass microspheres are nude silica glass microspheres.

9. The composition of claim 1 wherein the inert, ophthalmically-acceptable gel has an ophthalmically-acceptable viscosity, sufficient when placed in a mammalian eye to retain the microspheres on a corneal surface for at least a time to complete imaging thereof.

10. The composition of claim 1 wherein the inert, ophthalmically-acceptable gel is a carboxymethylcellulose gel.

11. The composition of claim 10 wherein the carboxymethylcellulose gel is a 1% carboxymethylcellulose gel.

12. The composition of claim 1 wherein the inert, ophthalmically-acceptable gel is a trehalose gel.

13. The composition of claim 12 wherein the trehalose gel is a 3% trehalose gel.

14. A method for enhancing reflection from a corneal surface for imaging of the cornea using light reflectance comprising:
dispensing into a mammalian eye prior to the imaging, a composition comprising microspheres of sterile, silica glass that enhance the reflectance of light from the corneal surface, dispersed in an inert, ophthalmically-acceptable gel having a viscosity suitable for conforming to at least the corneal surface of the eye and dispersing the microspheres thereover, wherein the composition comprises about 10% w/v or greater of the silica glass microspheres.

15. The method of claim 14 further comprising:
prior to the dispensing step, vigorously mixing the composition to disperse the microspheres in the gel, wherein the vigorous mixing disperses the microspheres without altering the viscosity of the gel.

16. The method of claim 14 further comprising:
following the imaging, rinsing the eye at least once with an ophthalmically-suitable rinse solution.

17. A method for enhancing corneal reflectance using an ophthalmic composition comprising:
vigorously mixing a composition comprising microspheres of sterile, silica glass that enhance the corneal reflectance in an inert, ophthalmically-acceptable gel having a viscosity suitable for conforming to at least the corneal surface of the eye, to disperse the microspheres in the gel wherein the vigorous mixing disperses the microspheres without altering the viscosity of the gel; and
dispensing a droplet of the composition onto at least a first mammalian eye within an optimal time following the vigorous mixing in which the microspheres are dispersed, wherein the composition comprises about 10% w/v or greater of the silica glass microspheres.

18. The method of claim 17 wherein if the optimal time is exceeded, the method further comprising:
allowing the microspheres to settle;
vigorously re-mixing the composition to disperse the microspheres in the gel wherein the vigorous mixing disperses the microspheres without altering the viscosity of the gel; and
dispensing a droplet of the composition onto at least a second mammalian eye within the optimal time following the vigorous re-mixing.

19. The method of claim 18 further comprising:
repeating the steps of settling and re-mixing prior to dispensing to subsequent mammalian eyes when the optimal time is exceeded.

20. The method of claim 18 wherein the optimal time is about 5 minutes.

21. The method of claim 17 wherein the vigorous mixing further comprises:
vortexing at about 3200 rpm for between about 5 minutes to about 10 minutes.

22. The method of claim 17 wherein the dispensing a droplet of the composition comprises:
dispensing about a 35 microliter droplet of the composition.

23. The method of claim 17 further comprising:
following the imaging, rinsing the eye at least once with an ophthalmically-suitable rinse solution.

24. The method of claim 23 wherein the rinsing the eye at least once comprises:
rinsing the eye at least twice with an ophthalmically-suitable rinse solution.

25. The composition of claim 3 wherein the incident light beam is at 1550 nm.

* * * * *